(12) United States Patent
Roth et al.

(10) Patent No.: US 6,656,203 B2
(45) Date of Patent: Dec. 2, 2003

(54) INTEGRAL VASCULAR FILTER SYSTEM

(75) Inventors: Noah M. Roth, Highland Park, NJ (US); Kirk Johnson, Weston, FL (US); David J. Wilson, Branchburg, NJ (US); Thomas Wiatrowski, Levittown, PA (US)

(73) Assignee: Cordis Corporation, Miami Lakes, FL (US)

( * ) Notice: Subject to any disclaimer, the term of this patent is extended or adjusted under 35 U.S.C. 154(b) by 15 days.

(21) Appl. No.: 09/907,860

(22) Filed: Jul. 18, 2001

(65) Prior Publication Data

US 2003/0015206 A1 Jan. 23, 2003

(51) Int. Cl.[7] .............................................. A61M 29/00
(52) U.S. Cl. ..................................................... 606/200
(58) Field of Search ................................ 606/159, 200, 606/113, 114, 127

(56) References Cited

U.S. PATENT DOCUMENTS

| | | |
|---|---|---|
| 3,952,747 A | 4/1976 | Kimmel, Jr. |
| 4,545,390 A | 10/1985 | Leary |
| 4,619,274 A | 10/1986 | Morrison |
| 4,665,905 A | 5/1987 | Brown |
| 4,688,553 A | 8/1987 | Metals |
| 4,727,873 A | 3/1988 | Mobin-Uddin |
| 4,925,445 A | 5/1990 | Sakamoto et al. |
| 4,969,890 A | 11/1990 | Sugita et al. |
| 4,984,581 A | 1/1991 | Stice |
| 4,991,602 A | 2/1991 | Amplatz et al. |
| 5,069,226 A | 12/1991 | Yamauchi et al. |
| 5,095,915 A | 3/1992 | Engelson |
| 5,171,383 A | 12/1992 | Sagaye et al. |
| 5,695,519 A | 12/1997 | Summers et al. |
| 5,769,816 A | 6/1998 | Barbut et al. |
| 5,814,064 A | 9/1998 | Daniel et al. |
| 5,827,324 A | 10/1998 | Cassell et al. |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 6,001,118 A | 12/1999 | Daniel et al. |
| 6,053,932 A | 4/2000 | Daniel et al. |
| 6,068,623 A | 5/2000 | Zadno-Azizi et al. |
| 6,069,814 A | 5/2000 | Liou et al. |
| 6,074,357 A | 6/2000 | Kaganov et al. |
| 6,152,946 A | 11/2000 | Broome et al. |
| 6,171,328 B1 | 1/2001 | Addis |
| 6,179,861 B1 | 1/2001 | Khosravi et al. |
| 6,191,365 B1 | 2/2001 | Avellanet |
| 6,203,561 B1 | 3/2001 | Ramee et al. |

FOREIGN PATENT DOCUMENTS

WO   WO 96/01591 A1   1/1996

Primary Examiner—Kevin T. Truong
(74) Attorney, Agent, or Firm—Paul A. Coletti

(57) ABSTRACT

A integral vascular filter system comprising a guidewire and an integral filter which can be used to capture embolic particulates during medical procedures, while allowing for continuous perfusion of blood, with minimal incremental blood flow turbulence. The vascular filter system addresses the clinical problem of minimizing profile or diameter, so as to enable or facilitate the crossing of a lesion or obstruction in the vessel, while also minimizing incremental blood flow turbulence which may result in thrombus formation.

28 Claims, 4 Drawing Sheets

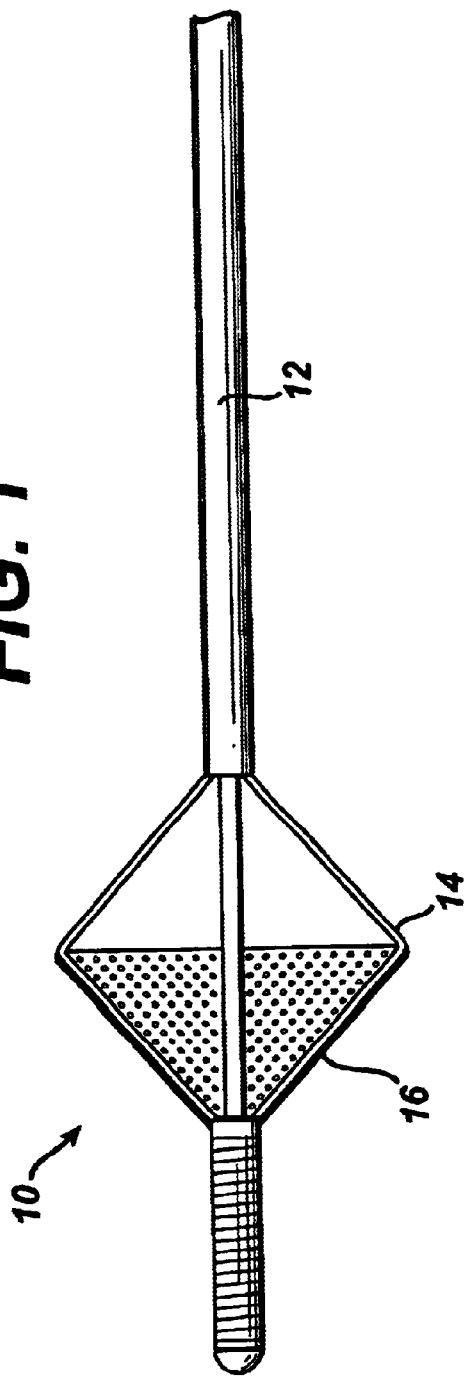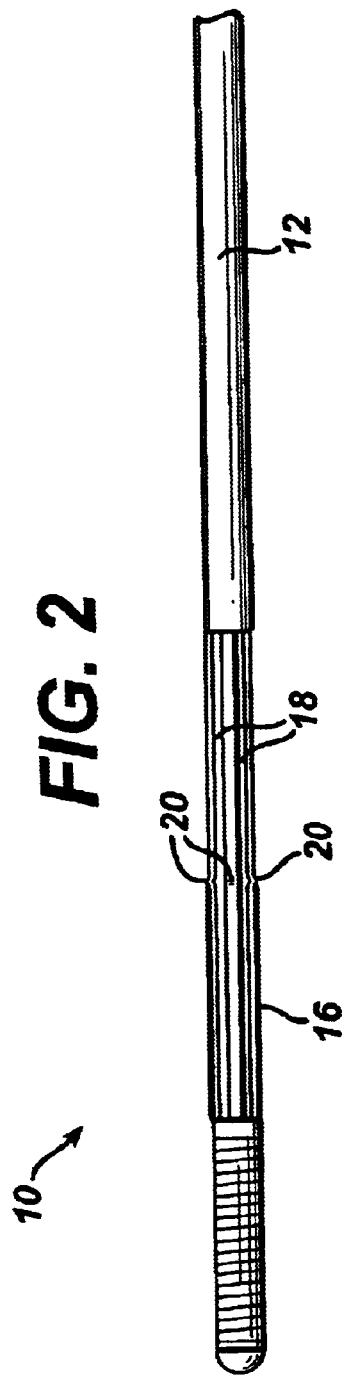

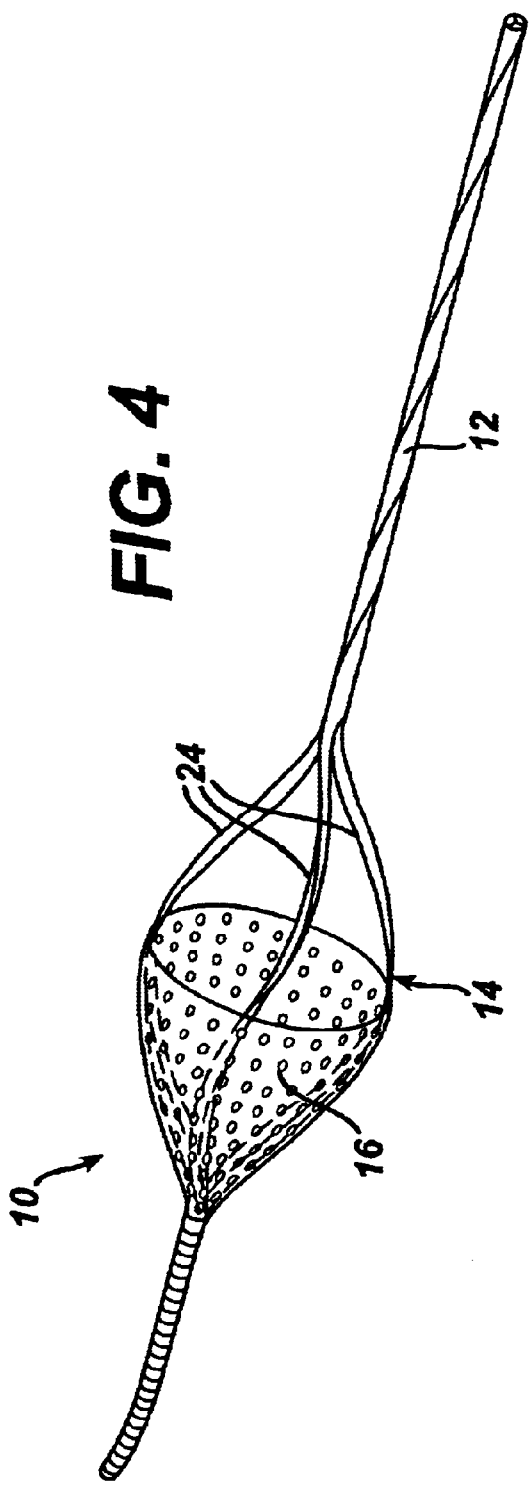
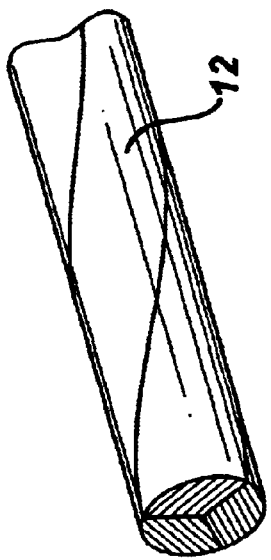

INTEGRAL VASCULAR FILTER SYSTEM

BACKGROUND

1. Field of the Invention

The present invention relates to the treatment of vascular disease, and more particularly to an integral vascular filter system for use during medical procedures.

2. Discussion of Related Art

Percutaneous transluminal coronary angioplasty (PTCA), stenting and atherectomy are therapeutic medical procedures used to increase blood flow through the coronary arteries. These procedures can often be performed as alternatives to coronary bypass surgery. PTA (percutaneous transluminal angioplasty) and stenting can often be performed as alternatives to carotid endarterectomy, and femoral-popliteal bypass procedures. In PTA or PTCA procedures, the angioplasty balloon is inflated within the stenosed vessel, at the location of an occlusion, in order to shear and disrupt the wall components of the vessel to obtain an enlarged lumen. In stenting, an endoluminal prosthesis is implanted in the vessel to maintain patency following the procedure. In atherectomy, a rotating blade is used to shear plaque from the arterial wall.

One of the complications associated with all these techniques is the accidental dislodgment of plaque, thrombus or other embolic particulates generated during manipulation of the vessel, thereby causing occlusion of the narrower vessels downstream and ischemia or infarct of the organ which the vessel supplies. Such emboli may be extremely dangerous to the patient, and may result in myocardial infarction, stroke or limb ischemia. In 1995, Waksman et al. disclosed that distal embolization is common after directional atherectomy in coronary arteries and saphenous vein grafts. See Waksman et al., American Heart Journal 129(3): 430–5 (1995). This study found that distal embolization occurs in 28% (31 out of 111) of the patients undergoing atherectomy. In January 1999, Jordan, Jr. et al. disclosed that treatment of carotid stenosis using percutaneous angioplasty with stenting procedure is associated with more than eight times the rate of microemboli seen using carotid endarterectomy. See Jordan, Jr. et al. Cardiovascular Surgery 7(1): 33–8 (1999). Microemboli, as detected by transcranial Doppler monitoring in this study, have been shown to be a potential cause of stroke. The embolic materials include calcium, intimal debris, atheromatous plaque, and thrombi.

In order to initiate these procedures, one must first introduce a guidewire into the lumen of the vessel to serve as a conduit for other interventional devices, such as angioplasty balloons and stent delivery systems. This guidewire must be advanced into position past the location of the occlusion. Guidewires must be capable of traversing tortuous pathways within the body, consisting of bends, loops and branches. For this reason, guidewires need to be flexible, but they should also be sufficiently stiff to serve as a conduit for other devices. In addition, they must be "torqueable" to facilitate directional changes as they are guided into position. Guidewires are well known in the art, and are typically made of stainless steel, tantalum or other suitable materials, in a variety of different designs. For example, U.S. Pat. Nos. 4,545,390 and 4,619,274 disclose guidewires in which the distal segment is tapered for greater flexibility. The tapered section may be enclosed in a wire coil, typically a platinum coil, which provides increased column strength, torqueability and radiopacity. A different design is identified in U.S. Pat. No. 5,095,915, where the distal segment is encased in a polymer sleeve with axially spaced grooves to provide bending flexibility. Another design is identified in U.S. Pat. No. 6,191,365, which discloses a multi-filament wire design.

Vascular filters are also well known in the art, especially vena cava filters, as illustrated in U.S. Pat. Nos. 4,727,873 and 4,688,553. There is also a substantial amount of medical literature describing various designs of vascular filters and reporting the results of clinical and experimental use thereof. See, for example, the article by Eichelter and Schenk, entitled "Prophylaxis of Pulmonary Embolism," Archives of Surgery, Vol. 97 (August, 1968). See, also, the article by Greenfield, et al, entitled "A New Intracaval Filter Permitting Continued Flow and Resolution of Emboli", Surgery, Vol. 73, No. 4 (1973).

Vascular filters are often used during a postoperative period, when there is a perceived risk of a patient encountering pulmonary embolism resulting from clots generated peri-operatively. Pulmonary embolism is a serious and potentially fatal condition that occurs when these clots travel to the lungs. The filter is therefore typically placed in the vena cava to catch and trap clots before they can reach the lungs.

Many of the vascular filters in the prior art are intended to be permanently placed in the venous system of the patient, so that even after the need for the filter has passed, the filter remains in place for the life of the patient. U.S. Pat. No. 3,952,747 describes a stainless steel filtering device that is permanently implanted transvenously within the inferior vena cava. This device is intended to treat recurrent pulmonary embolism. Permanent implantation is often deemed medically undesirable, but it is done because filters are implanted in patients in response to potentially life-threatening situations.

To avoid permanent implantation, it is highly desirable to provide an apparatus and method for preventing embolization associated with angioplasty, stenting or other procedures. In particular, it is desirable to provide a device which can be temporarily placed within the vascular system to collect and retrieve plaque, thrombus and other embolic particulates which have been dislodged and/or developed as a result of angioplasty, stenting or other procedures. Such a device is removed at the end of the procedure. U.S. Pat. Nos. 5,814,064 and 5,827,324 describe such a device, wherein the filter is expanded through the introduction of a fluid or a gas. U.S. Pat. No. 5,910,154 describes a filter, which expands through the use of a spring-based actuator. U.S. Pat. No. 6,053,932 describes a filter, which expands through the use of a cinch assembly. U.S. Pat. Nos. 6,179,861 and 6,001,118 describe guidewire-based filters where the filter resembles a windsock and is supported by one or more articulated support hoops.

One concern commonly encountered with all these devices is that the profile or outer diameter of the wire incorporating the filter tends to be substantially larger than the wire itself. This larger profile makes it difficult to cross the lesion or obstruction in the vessel. If the guidewire with filter cannot cross the lesion or obstruction, the procedure must be done without a filter in place. This can lead to accidental dislodgment of plaque, thrombus or other embolic particulates generated during manipulation of the vessel, thereby causing occlusion of the narrower vessels downstream and ischemia or infarct of the organ which the vessel supplies. Such emboli may be extremely dangerous to the patient, and may result in myocardial infarction, stroke or limb ischemia.

Another concern commonly encountered with all these devices is that the pores on the filter covering can become clogged with embolic particulates or clotted blood, thereby preventing perfusion of distal vessels during the procedure. The filter must then be collapsed, removed and replaced in order to continue the procedure. This complicates the procedure, and also temporarily leaves the site without a filter. One factor contributing to this problem is incremental blood flow turbulence and subsequent thrombus formation due to the angulation of the filter pores relative to the flow of blood.

The prior art makes reference to the use of alloys such as Nitinol (Ni—Ti alloy), which have shape memory and/or superelastic characteristics, in medical devices that are designed to be inserted into a patient's body. The shape memory characteristics allow the devices to be deformed to facilitate their insertion into a body lumen or cavity, and then, when heated within the body, to return to their original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

The prior art makes reference to the use of metal alloys having superelastic characteristics in medical devices which are intended to be inserted or otherwise used within a patient's body. See for example, U.S. Pat. No. 4,665,905 (Jervis).

Some guidewire designs have recommended the use of superelastic alloys. For example, U.S. Pat. No. 4,925,445 discloses a guidewire where the distal segment, and at least one portion of the proximal segment, are made from a superelastic alloy like Nitinol, where the transformation temperature from austenite to martensite occurs at 10° C. or below. Also, U.S. Pat. No. 4,984,581 discloses a guidewire having a core of shape memory alloy, where the shape memory properties of the alloy provide both tip-deflection and rotational movement in response to a controlled themal stimulus.

However, the prior art has yet to disclose any guidewires, made from Nitinol or other suitable materials, incorporating vascular filters, which can be used to address the clinical problem of minimizing profile or diameter, so as to facilitate the crossing of a lesion or obstruction in the vessel. Also, the prior art has yet to disclose any vascular filters incorporating porous coverings designed to minimize incremental blood flow turbulence and subsequent thrombus formation, which can clog the filter and prevent perfusion of distal vessels.

SUMMARY OF THE INVENTION

The present invention provides for an integral vascular filter system, which can be used to address the clinical problem of minimizing profile or diameter to enable or facilitate the crossing of a lesion or obstruction in the vessel, and which overcomes many of the deficiencies associated with the prior art devices, as briefly described above. The present invention also provides for an integral vascular filter system incorporating a metallic mesh porous covering, which can be used to address the clinical problem of minimizing incremental blood flow turbulence, thrombus formation and clogged filters, and which overcomes many of the deficiencies of prior art devices, as briefly described above.

In accordance with one aspect, the present invention is directed to an integral vascular filter system comprising a guidewire, a prescribed filter shape in the distal portion of the guidewire, and a porous covering attached to the distal portion of the guidewire. The prescribed filter shape may be formed from a plurality of slots comprising at least one articulation point, in the distal portion of said guidewire. The distal portion of the guidewire has a smaller first diameter for insertion into a vessel, and a second larger diameter for expanding to substantially equal the diameter of the lumen of the vessel, and to be placed in generally sealing relationship with the lumen. The system further comprises actuating means for causing the distal portion of the guidewire to move from the smaller first diameter, to the larger second diameter and prescribed filter shape, and back.

In accordance with another aspect, the present invention is directed to an integral vascular filter system comprising a multi-filament guidewire, a prescribed filter shape in the distal portion of the guidewire, and a porous covering attached to the distal portion of the guidewire. The prescribed filter shape may be formed from the multi-filaments of the distal portion of the guidewire. The distal portion of the guidewire has a smaller first diameter for insertion into a vessel, and a second larger diameter for expanding to substantially equal the diameter of the lumen of the vessel, and to be placed in generally sealing relationship with the lumen. The system further comprises actuating means for causing the distal portion of the guidewire to move from the smaller first diameter, to the larger second diameter and prescribed filter shape, and back.

The integral vascular filter system enables or facilitates crossing lesions or obstructions in vessels. The filter is then actuated, and used to capture embolic particulates released during a medical procedure. The filter is then collapsed, and the system is removed from the patient.

In accordance with another aspect, the present invention is directed to an integral vascular filter system comprising a guidewire, a prescribed filter shape in the distal portion of the guidewire, and a metallic mesh porous covering attached to the distal portion of the guidewire. The distal portion of the guidewire has a smaller first diameter for insertion into a vessel, and a second larger diameter for expanding to substantially equal the diameter of the lumen of the vessel, and to be placed in generally sealing relationship with the lumen. The system further comprises actuating means for causing the distal portion of the guidewire to move from the smaller first diameter to the second larger diameter and prescribed filter shape, and back. The metallic mesh porous covering comprises parallelogram-shaped pores with acute and obtuse angles, which are designed to minimize incremental blood flow turbulence and subsequent thrombus formation, which can clog the filter and prevent perfusion of distal vessels.

The integral vascular filter system enables or facilitates crossing lesions or obstructions in vessels. The filter is then actuated, and used to capture embolic particulates released during a medical procedure. The metallic mesh porous covering minimizes incremental blood flow turbulence and subsequent thrombus formation, which can clog the filter and prevent perfusion of distal vessels. The filter is then collapsed, and the system is removed from the patient.

The advantage of the present invention is that the low profile or minimized diameter of the integral vascular filter system can enable or facilitate the crossing of lesions or obstructions in the vessel, which may not be crossable with other filter devices. Another advantage of the present invention is that the metallic mesh porous covering on the filter can minimize incremental blood flow turbulence and subsequent thrombus formation, thereby avoiding clogging of the filter during the procedure.

BRIEF DESCRIPTION OF DRAWINGS

The foregoing and other aspects of the present invention will best be appreciated with reference to the detailed description of the invention in conjunction with the accompanying drawings, wherein:

FIG. 1 is a simplified, cross-sectional view of an exemplary embodiment of the integral vascular filter system with the filter in the open position, in accordance with the present invention.

FIG. 2 is a simplified cross-sectional view of an exemplary embodiment of the integral vascular filter system with the filter is in the closed position, in accordance with the present invention.

FIG. 4 is an simplified, cross-sectional view of an exemplary embodiment of the integral vascular filter system made from multi-filament wire, with the filter in the open position, in accordance with the present invention.

FIG. 5 is an enlarged, partial cross-sectional view of an exemplary embodiment of the integral vascular filter system made from multi-filament wire, in accordance with the present invention.

DETAILED DESCRIPTION OF THE PREFERRED EMBODIMENTS

The integral vascular filter system of the present invention is designed to address the clinical problem of minimizing profile or diameter to enable or facilitate the crossing of a lesion or obstruction in the vessel. The present invention also provides for an integral vascular filter system incorporating a metallic mesh porous covering, which can be used to address the clinical problem of minimizing incremental blood flow turbulence, thrombus formation and clogged filters. The device comprises a guidewire having an outer diameter, a distal portion and a proximal portion, with the distal portion having a distal end, a midpoint and a proximal end; a prescribed filter shape in the distal portion of the guidewire, the distal portion having a having a smaller first diameter for insertion into a vessel, and a larger second diameter for expanding to substantially equal the diameter of the lumen and to be placed in generally sealing relationship with the lumen; a porous covering having a distal end and a proximal end, with the distal end of the porous covering attached near the distal end of the distal portion of the guidewire, and the proximal end of the porous covering attached near the midpoint of the distal portion of the guidewire; and actuating means for causing the distal portion of the guidewire to move from the smaller first diameter to the larger second diameter and the prescribed filter shape, and back to the smaller first diameter. The integral vascular filter may be of sufficiently small profile or diameter to cross the lesion or occlusion, and may be placed distal to the occlusion to collect embolic particulates released during the procedure. Thereafter, the filter may be closed and removed from the patient, with the embolic particulates trapped within the filter.

While the present invention may be realized in a number of exemplary embodiments, for ease of explanation, three exemplary embodiment will be described in detail. Referring to the figures wherein like numerals indicate the same element throughout the views, there is shown in FIG. 1, an integral vascular filter system 10 made in accordance with the present invention. The integral vascular filter system 10 comprises a guidewire 12, which comprises a guidewire distal portion 14 with a prescribed filter shape. The guidewire distal portion 14 comprises a porous covering 16 attached to the guidewire distal portion 14. As illustrated in FIG. 1, when the guidewire distal portion 14 achieves its larger second diameter and prescribed filter shape, the filter is in the open position. As illustrated in FIG. 2, when the guidewire distal portion 14 achieves its smaller first diameter, the filter is in the closed position.

Figure 3:
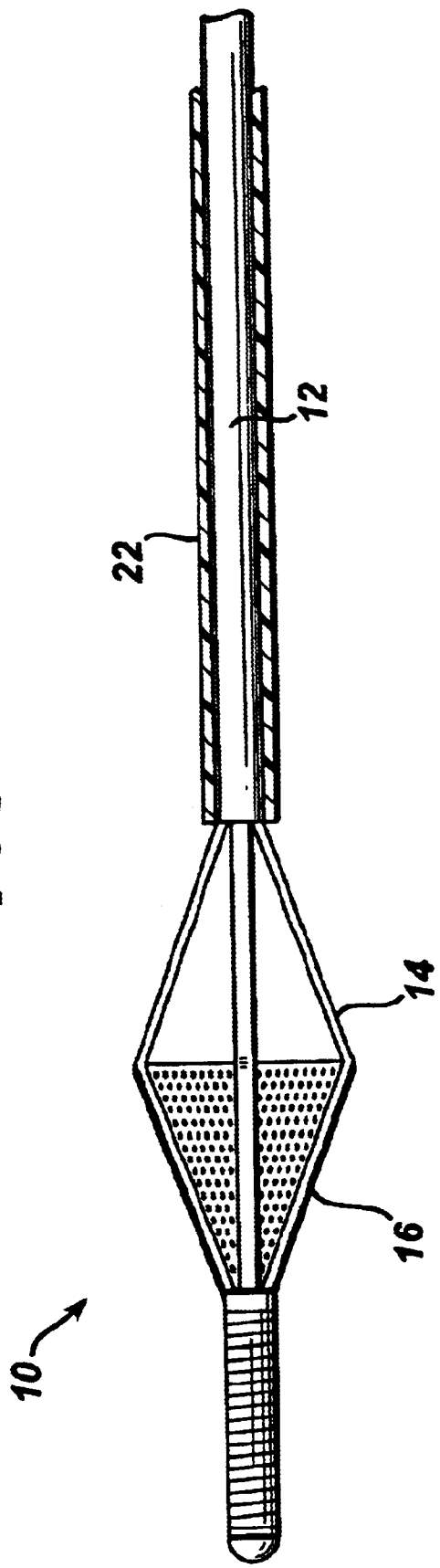
FIG. 3 is a simplified cross-sectional view of an exemplary embodiment of the integral vascular filter system with the filter is in the closed position and actuating means in place, in accordance with the present invention.

In accordance with one exemplary embodiment, as illustrated in FIG. 2, the guidewire distal portion 14 may comprise a plurality of slots 18. The plurality of slots 18 may comprise at least one articulation point 20. As illustrated in FIG. 3, the integral vascular filter system 10 may also comprise actuating means 22 for causing the guidewire distal portion 14 to move from a smaller first diameter to a larger second diameter and prescribed filter shape. As illustrated in FIG. 3, the actuating means 22 may be a sheath which is advanced over the guidewire distal portion 14 to cause the guidewire distal portion 14 to move from a larger second diameter and prescribed filter shape, to a smaller first diameter. The sheath may also be retracted to cause the guidewire distal portion to move from a smaller first diameter, to a larger second diameter and prescribed filter shape.

In accordance with another exemplary embodiment, as illustrated in FIGS. 4 and 5, the guidewire 12 may be a multi-filament wire. As illustrated in FIG. 4, the guidewire distal portion 14 has a prescribed filter shape formed from the filaments 24 of the multi-filament wire. The guidewire distal portion 14 comprises a porous covering 16 attached to the guidewire distal portion 14. As illustrated in FIG. 4, when the guidewire distal portion 14 achieves its larger second diameter and prescribed filter shape, the filter is in the open position.

As illustrated in FIGS. 1, 2, 3, 4 and 5, the integral vascular filter system 10 may be used to cross lesions or obstructions in a vessel, and may then be used to collect and trap embolic particulates released during a medical procedure. The guidewire 12 is introduced into the lumen of the vessel, with the distal portion 14 in the closed position. A sheath 22 may be used to prevent actuation of the filter, while the integral vascular filter system 10 is being positioned in the vessel, with the guidewire distal portion 14 positioned past the lesion or occlusion. Other actuating means, such as guide catheters, other procedural devices or core wires, may also be employed. Once the integral vascular filter system 10 is in position past the lesion or occlusion, the actuating means 22 may be employed to allow the guidewire distal portion 14 to achieve its larger second diameter and prescribed shape, with the porous covering 16 attached to the guidewire distal portion 14. At this point, other procedural devices, such as angioplasty balloons and stent delivery systems, may be introduced over the guidewire 12, to therapeutically treat the lesion or occlusion. Any embolic particulates released during the procedure may be captured in the porous covering 16 on the guidewire distal portion 14, while the pores in the porous covering allow distal perfusion of blood. When the therapeutic treatment of the lesion or occlusion is complete, the procedural devices may be withdrawn, and actuating means 22 may be used to return the guidewire distal portion 14 to its smaller first diameter. The guidewire 12 may then be removed from the lumen of the vessel.

The guidewire 12 may be made from any number of suitable materials, and is preferably made from stainless steel or polymeric material, and is more preferably made from a superelastic alloy such as Nitinol. The guidewire distal portion 14 may comprise any number or configuration of slots, and may preferably comprise longitudinal slots. The guidewire 12 may be a multi-filament wire, and may comprise straight or, more preferably, twisted multi-filaments. The porous covering 16 may be made from any number of suitable materials, and is preferably made from a flexible polymeric material with elastomeric properties chosen from a group consisting of polyurethane, polyethylene, silicone, nylon, polypropylene, PVC, or a co-polymer or mixture thereof. The porous covering 16 may comprise any number and configuration of pores and preferably comprises regularly-spacer laser-formed holes wherein the pore size is from about 20 to about 300 microns.

Figure 6:
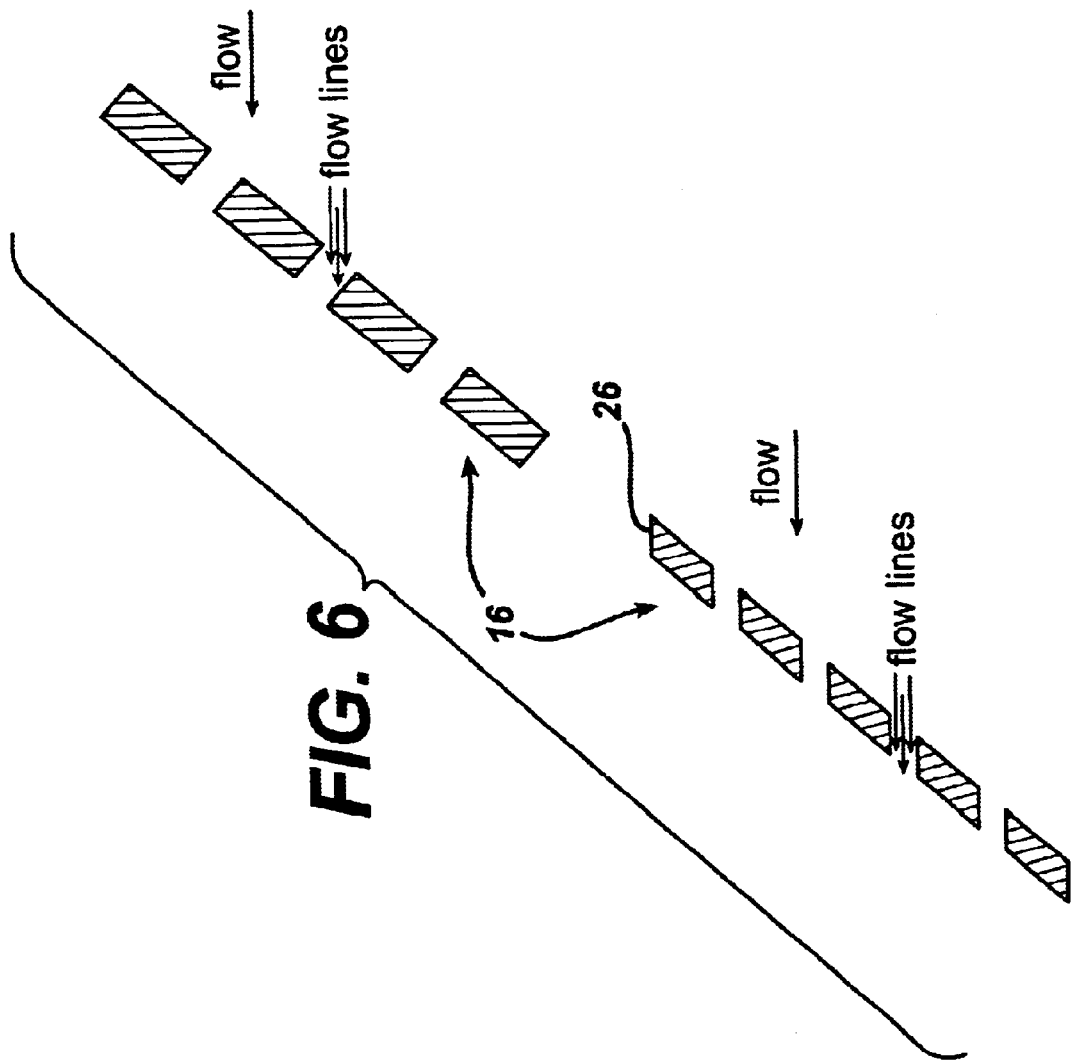
FIG. 6 is an enlarged, partial top view of an exemplary embodiment of the integral vascular system, with the metallic mesh porous covering comprising parallelogram-shaped pores with acute and obtuse angles, as compared to rectangle-shaped pores, in accordance with the present invention.

In accordance with another exemplary embodiment, as illustrated in FIG. 6, the porous covering 16 may be a metallic mesh which may comprise parallelogram-shaped pores with acute and obtuse angles 26. As illustrated in FIG. 6, while rectangular-shaped pores may cause incremental blood flow turbulence and subsequent thrombus formation, which may clog the porous covering 16, parallelogram-shaped pores with acute and obtuse angles 26 may avoid incremental blood flow turbulence due to their angulation relative to blood flow. The metallic mesh may be made from any number of suitable materials, and is preferably made from a superelastic alloy such as Nitinol.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to include all modifications that may fall within the scope of the appended claims.

That which is claimed is:

1. A vascular filter system for insertion into a lumen of a vessel, said vascular filter system comprising:
    a) a guidewire having a distal end and a proximal end, a distal portion and a proximal portion, with said distal portion having a distal end, a midpoint and a proximal end;
    b) a prescribed filter shape integral with and placed within said distal portion of said guidewire, said distal portion having a smaller first diameter for insertion into said lumen of said vessel, and a larger second diameter for expanding to substantially equal the diameter of said lumen and to be placed in generally sealing relationship with said lumen;
    c) a porous covering having a distal end and a proximal end, with said distal end of said porous covering attached near said distal end of said distal portion of said guidewire, and said proximal end of said porous covering attached near said midpoint of said distal portion of said guidewire, and;
    d) actuating means for causing said distal portion of said guidewire to move between said smaller first diameter, and said larger second diameter and said prescribed filter shape wherein said actuating means is a generally solid core wire.

2. The vascular filter system according to claim 1, wherein said guidewire is made from Nickel-titanium alloy.

3. The vascular filter system according to claim 1, wherein said guidewire is made from stainless steel alloy.

4. The vascular filter system according to claim 1, wherein said guidewire is made from polymeric material.

5. The vascular filter system according to claim 1, wherein said distal portion of said guidewire comprises a plurality of slots.

6. The vascular filter system according to claim 5, wherein said plurality of slots comprises a proximal end and a distal end, and at least one articulation point therebetween.

7. The vascular filter system according to claim 6, wherein said at least one articulation point is a hinge.

8. The vascular filter system according to claim 5, wherein said prescribed filter shape comprises said plurality of slots in said distal portion of said guidewire.

9. The vascular filter system according to claim 1, wherein said guidewire is a multi-filament guidewire.

10. The vascular filter system according to claim 9, wherein said prescribed filter shape comprises said multi-filaments of said distal portion of said guidewire.

11. The vascular filter system according to claim 1, wherein said guidewire is a twisted multi-filament guidewire.

12. The vascular filter system according to claim 1, wherein a pore size of said porous covering is from about 20 to about 300 microns.

13. The vascular filter system, according to claim 1, wherein said porous covering is a flexible polymeric material comprising regularly-spaced laser-formed holes therein.

14. The vascular filter system according to claim 13, wherein said flexible polymeric material is chosen from a group consisting of polyurethane, polyethylene, silicone, nylon, polypropylene, PVC, or a co-polymer or mixture thereof.

15. The vascular filter system according to claim 13, wherein said flexible polymeric material is an elastomeric material capable of stretching to achieve said larger second diameter of said filter.

16. The vascular filter system according to claim 13, wherein a pore size of said porous covering is from about 20 to about 300 microns.

17. The vascular filter system according to claim 1, wherein said porous covering is a superelastic metallic mesh.

18. The vascular filter system according to claim 17, wherein said superelastic metallic mesh comprises parallelogram-shaped pores, comprising acute and obtuse angles.

19. The vascular filter system according to claim 17, wherein a pore size of said porous covering is from about 20 to about 300 microns.

20. The vascular filter system according to claim 17, wherein said porous covering is made from Nickel-Titanium alloy.

21. The vascular filter system, according to claim 1, wherein said actuating means is a sheath.

22. The vascular filter system, according to claim 1, wherein said actuating means is a guide catheter.

23. The vascular filter system according to claim 22, wherein a pore size of said parallelogram-shaped pores is from about 20 to about 300 microns.

24. The vascular filter system according to claim 22, wherein said superelastic metallic mesh is made from Nickel-Titanium alloy.

25. A vascular filter system for insertion into a lumen of a vessel, said vascular filter system comprising:
  a) a guidewire having a distal end and a proximal end, a distal portion and a proximal portion, with said distal portion having a distal end, a midpoint and a proximal end;
  b) a prescribed filter shape integral with and placed within said distal portion of said guidewire, said distal portion having a smaller first diameter for insertion into said lumen of said vessel, and a larger second diameter for expanding to substantially equal the diameter of said lumen and to be placed in generally sealing relationship with said lumen;
  c) a porous covering having a distal end and a proximal end with said distal end of said porous covering attached near said distal end of said distal portion of said guidewire, and said proximal end of said porous covering attached near said midpoint of said distal portion of said guidewire, and;
  d) actuating means for causing said distal portion of said guidewire to move between said smaller first diameter, and said larger second diameter and said prescribed filter shaped; and
    wherein said actuating means is a generally solid core wire having a proximal end and a distal end.

26. The vascular filter system, according to claim 25 wherein said prescribed filter shape attains said larger second diameter when said core wire is slidably retracted through said guidewire.

27. A method for capturing embolic particulates within the lumen of a vessel during a medical procedure, while allowing for continuous perfusion of blood, comprising the steps of:
  a) providing a guidewire comprising a distal portion and a proximal portion, with said distal portion having a distal end, a midpoint and a proximal end; a prescribed filter shape in said distal portion of said guidewire, said distal portion of said guidewire having a smaller first diameter for insertion into a vessel, and a second larger diameter for expanding to substantially equal the diameter of said lumen and to be placed in generally sealing relationship with said lumen; a porous covering having a distal end and proximal end, with said distal end of said porous covering integral with and placed within near said distal end of said distal portion of said guidewire, and said proximal end of said porous covering attached near said midpoint of said distal portion of said guidewire; and actuating means for causing said distal portion of said guidewire to move between said smaller first diameter, and said larger second diameter and prescribed filter shape wherein said actuating means a generally solid core wire;
  b) inserting said guidewire into said lumen of said vessel until said distal portion of said guidewire is positioned past an occlusion in said vessel;
  c) employing said actuating means to cause said distal portion of said guidewire to achieve said larger second diameter and said prescribed shape;
  d) advancing additional devices over said guidewire, and positioning said devices at the site of said occlusion in said vessel;
  e) performing additional procedures to therapeutically treat said occlusion in said vessel;
  f) capturing embolic particulates generated by said procedures, in said porous covering on said distal portion of said guidewire;
  g) removing said additional devices from said guidewire;
  h) employing said actuating means to cause said distal portion of said guidewire to achieve said smaller first diameter;
  i) removing said guidewire from said lumen of said vessel, with said embolic particulates captured in said porous covering.

28. A vascular filter comprising:
  a) a guidewire having an outer diameter, a distal portion and proximal portion, with said distal portion having a distal end, a midpoint and proximal end;
  b) a filter placed integral with and placed within said distal portion of said guidewire, said filter distal portion having a shape with smaller first diameter for insertion into said lumen of said vessel, and a larger second diameter placed in generally sealing relationship with a body lumen;
  c) a porous covering having a distal end and a proximal end, with said distal end of said porous covering attached near said distal end of said distal portion of said guidewire; and
  d) actuating means for causing said distal portion of said guidewire to move between said smaller first diameter and said larger second diameter wherein said actuating means is a generally solid core wire.

* * * * *